United States Patent [19]

Hermann et al.

[11] Patent Number: 4,757,010

[45] Date of Patent: Jul. 12, 1988

[54] PRODUCTION OF CLOSTRIDIUM ACETOBUTYLICUM MUTANTS OF HIGH BUTANOL AND ACETONE PRODUCTIVITY, THE RESULTANT MUTANTS AND THE USE OF THESE MUTANTS IN THE JOINT PRODUCTION OF BUTANOL AND ACETONE

[75] Inventors: Monique Hermann, Paris; Francoise Fayolle, Malakoff; Rémy Marchal, Chatou, all of France

[73] Assignee: Institut Francais Du Petrole, Rueil-Malmaison, France

[21] Appl. No.: 810,841

[22] Filed: Dec. 19, 1985

Related U.S. Application Data

[63] Continuation of Ser. No. 473,186, Mar. 8, 1983, abandoned.

[30] Foreign Application Priority Data

Mar. 8, 1982 [FR] France ............... 82 03980

[51] Int. Cl.$^4$ ............... C12P 7/28; C12P 7/16; C12N 1/20; C12R 1/145
[52] U.S. Cl. ............... 435/150; 435/160; 435/253; 435/842
[58] Field of Search ............... 435/172, 245, 148, 253, 435/842, 150, 160, 170

[56] References Cited

U.S. PATENT DOCUMENTS 4,352,880 10/1982 Awerbuch ............... 435/39

FOREIGN PATENT DOCUMENTS 0035288 8/1979 Japan ............... 935/38
0278307 10/1927 United Kingdom ............... 435/245
1021721 3/1966 United Kingdom ............... 935/38

OTHER PUBLICATIONS

Demain, Genetics of Industrial Microorganisms, vol. I, Elsevier Publishing Co., N.Y., (1973) pp. 21–23.
The Microbial World, 4th Ed., 1976, Prentice-Hall International, Inc., London, pp. 407 and 409.

*Primary Examiner*—Robert J. Warden
*Assistant Examiner*—William J. Herald
*Attorney, Agent, or Firm*—Millen & White

[57] ABSTRACT

The *Clostridium acetobutylicum* mutant IFP 904 (ATCC 39058) is obtained by spreading a culture of a strain of *Clostridium acetobutylicum* at the surface of a solid culture medium containing n-butanol at a specified concentration, growing the strain in the presence of a mutagenic agent and recovering a strain of increased resistance to n-butanol. The resultant mutant can be used to produce a mixture of butanol and acetone of increased concentration.

3 Claims, No Drawings

PRODUCTION OF CLOSTRIDIUM ACETOBUTYLICUM MUTANTS OF HIGH BUTANOL AND ACETONE PRODUCTIVITY, THE RESULTANT MUTANTS AND THE USE OF THESE MUTANTS IN THE JOINT PRODUCTION OF BUTANOL AND ACETONE

This application is a continuation of application Ser. No. 473,186 filed Mar. 8, 1983.

BACKGROUND OF THE INVENTION

The acetone-butanol fermentation, known for a long time, results in the conversion of various sugars to a mixture of industrial interest: butanol, acetone and ethanol (ABE); it thus constitutes a particularly advantageous process for obtaining the main product: n-butanol. The advantage of this manner of obtaining components of alternate fuels has also been disclosed in the French patent application Nos. 80/12822 and 80/17147 of Institut Francais du Petrole. The main limitation of this fermentation has however been, up to now, the relatively low concentration of the resultant products which is generally not higher, under the best conditions, than a total of 20 g/l, typically 10-13 g/l of n-butanol, 4-7 g/l of acetone and 0-2 g/l of ethanol, as shown in the synthesis publications of M. T. Walton and J. L. Martin (Microbial Fermentation, 2nd edition, vol. 1, Academic Press, 1979, p. 187-209) and S. C. Prescott and C. G. Dunn (Industrial Microbiology, Mc Graw Hill, 1959, p. 250-293).

SUMMARY OF THE INVENTION

The object of this invention is to disclose a method for producing mutants of *Clostridium acetobutylicum* which, when grown under appropriate conditions, yield ABE concentrations far higher than those produced by the mother strain and which are above 20 g/l. These mutants are called ABE high productivity mutants.

The use of conventional mutagenesis techniques met with several difficulties, when applied to *Clostridium acetobutylicum*. The first difficulty lies in the strictly anaerobic character of this bacterium. Normal growing of colonies on a solid nutrient medium, a basic technique used in microbiology to isolate, select and purify microorganism strains, is only obtained if particular care is taken in order to operate in a completely oxygen-free environment. The operations have thus been conducted in an anaerobic glove-box with previously reduced media, for example under the conditions disclosed by L. V. Holdeman, E. P. Cato and W. E. C. Moore (Anaerobe Laboratory Manual, 4th edition, 1977, Virginia Polytechnic Institute, Blacksburg, Va, p. 144).

Numerous mutagenesis techniques have been used under the above conditions. First, several mutagenic agents have been tested, specially ethylmethylsulfonate (EMS), N-methyl N'-nitro N-nitrosoguanidine (NG), ICR 191, nitrous acid and nitroquinoline-N-oxide. Then the manner these mutagenic agents are used has been modified. The most usual technique consists of subjecting a microbial suspension to mutagenesis in a liquid medium by exposing it, at a given concentration and for a given time, to the selected mutagenesis agent. The medium is then centrifuged and the microbial suspension is washed to eliminate the mutagenesis agent; it is then cultured and spread out on a solid nutritive medium (Petri dishes) to obtain individual colonies of surviving microorganisms; mutants having the desired characteristics are then selected among those colonies. By varying the mutagenesis time and the concentration of the mutagenesis agent, the mutation rate and the mortality rate of the microorganisms is then modified and the conditions leading to the most favorable mutation rate are selected. This well known technique has been described in specialized books, particularly by J. H. Miller (Experiments in molecular genetics. Cold Spring Harbor, 1972, p. 125).

It has been found, that irrespective of the mutagenesis agent, the use of this technique results in a very low production of mutants, which in no case are ABE high productivity mutants.

According to the mutagenesis technique of the invention, the mutagenesis is effected in one step in a solid medium, in a varied concentration range, and the desired mutants are isolated. This result has been obtained by spreading out liquid cultures of *Clostridium acetobutylicum* in the growing state on a solid nutritive medium containing n-butanol, for example, in Petri dishes. A concentration gradient of the mutagenesis agent is obtained by placing the mutagenesis agent at one point, for example, at the center of each dish; the mutagenesis agent, preferably nitrosoguanidine (NG) thus creates the desired gradient by progressive diffusion of the mutagenesis agent. The ABE high productivity mutants are obtained by selecting butanolresistant mutants, expecting the latter to tolerate a greater butanol accumulation in the ABE production experiments. Thus, butanol has been added to the above mentioned Petri dishes at concentrations which increase from dish to dish, and all of which inhibit the mother strain. After incubation, under the known conditions for incubating *C. acetobutylicum*, these Petri dishes contain isolated n-butanol-resistant colonies. The ability of these mutants to produce ABE has been tested and it has been found that most of them were high ABE producers. When adequate butanol concentrations were used in the Petri dishes, many mutants were obtained with various *C. acetobutylcium* strains. As a rule, the technique is reproducible. However certain *C. acetobutylicum* strains do not naturally supply sufficiently small isolated colonies having a distinct contour. In the latter case, the production of mutants has required the isolation of spontaneous variants forming colonies having sufficiently distinct contours to be easily handled as described above.

The reasons why the above technique to isolate ABE highly producing mutants is efficient have not been fully understood. It seems that this technique, which only comprises handlings effected in an anaerobic chamber, are better adapted to conditions of complete anaerobiose. It is also observed that the selection test (resistance to butanol) is a good test for selecting mutants having a high ABE productivity, which shows that these two properties are associated. As concerns the mutagenic agent, it must be noted that all the mutagenic agents are not equivalent and that, for example, the use of EMS, in the same conditions, has given results substantially not as good as nitroguanidine. The mutants which are the object of the present invention have thus been obtained by using, as the selection test, resistance to butanol after a particular mutagenic treatment. Mutants have been obtained from different mother-strains of *Clostridium acetobutylicum*, particularly strains previously isolated in the laboratory from natural media. They are characterized by their resistance to butanol (and other solvents) as well as by their productivity of solvents (butanol and acetone) which are greater then those of the mother-strain.

It has also been observed that the resultant mutants have sporulation properties differing from those of the mother-strain since the proportion of the bacteria able to form spores at the end of the culture was lower in the mutants than in the wild strain.

The following examples illustrate the method to obtain mutants and their characterization in the case of a strain isolated in the laboratory (strain IFP 903) and used for fermenting Jerusalem artichoke liquor. The obtainment of mutants and their performances do not depend on the use of a specific sugar substrate and have been observed with the various sugars usable by *Clostridium acetobutylicum*, specially glucose, fructose, saccharose, starch, cellobiose, xylose and hydrolysates of lignocellulosic materials such as corn stalks.

The properties of the strain IFP 903 have led to its identification as a *Clostridium acetobutylicum* strain and are given hereinafter. The mutants obtained as described above and illustrated in example 1 have the same taxonomic characteristics as the mother-strain except, as mentioned above, a lower sporulation rate than the mother-strain.

PROPERTIES OF THE STRAIN IFP 903 OF CLOSTRIDIUM ACETOBUTYLICUM

Morphology: Small rods with round ends, motionless, isolated, Gram positive with frequently subterminal, sometimes terminal oval spores, inflated sporange.

Culture: PY-glucose broth (PY medium described by Miller, cited above): Strongly turbid with gas Py broth: weakly turbid with gas agar (PY+-glucose): white round colonies of 1-2 mm diameter, turning yellow on ageing.

The growth occurs under strictly anaerobic conditions. The sugars are mainly converted to butanol and acetone (and a little ethanol). Volatile acids (acetic and butyric acids) are formed in smaller amounts. The resultant gas consists of carbon dioxide and hydrogen.

Glucides and other carbon-containing substrates

Vigorous growth with production of gas and acid on: raffinose, lactose, melibiose, levulose, maltose, trehalose, cellobiose, mannose, xylose, salicine, galactose, glucose, β-methylglucoside, starch, saccharose, mannitol.

Less vigorous growth with production of gas and acid on: inositol, esculine, α-methyl glucoside.

Low growth, little gas and acid: sorbitol, rhamnose. Not utilized: erythritol, arabinose, ribose, glycerol, pectine.

Proteins: milk: coagulated; casein; not utilized; serum: not utilized; gelatine: not utilized.

Lipids: lecithinase: negative result; tributyrine: no culture.

Other properties: hemolysis: none; urea: negative or very weakly positive; sulfites: reduced; H₂S production: positive; nitrates: not utilized; indole: not formed; acetoine: not formed.

These properties, as compared to those given by Mc Coy et al. (E. E. B. Mc Coy, E. B. Fred, W. H. Peterson and E. G. Hastings, Journal of Infectious Diseases—19-26—39, 457-483) for *Clostridium acetobutylicum* lead one to classify the strain IFP 903 and the strains obtained from the latter by the above method in the species *Clostridium acetobutylicum*

EXAMPLE 1

(1) Method for preparing mutants of *Clostridium acetobutylicum* resistant to butanol A strain of *Clostridium acetobutylicum* (IFP No. 903) was grown for a night in an anaerobic chamber on a complete medium, the PY medium described by Miller as hereinbefore mentioned. The carbon source was glucose in a proportion of 10 g/l.

The strain was grown again on the next morning in 10 ml of fresh PY medium. On the same day, dishes of agar-containing PY medium were prepared in the anaerobic chamber at increasing concentrations of n-butanol: 5, 7, 10 and 12 g per liter. After growing of the strain (8 h), 0.1 ml of culture was spread out on each dish. 15 minutes later, a crystal of nitrosoguanidine was set at the center of each dish. The boxes were incubated at 32° C. for 3 days in the anaerobic chamber.

The partial inhibiting effect of nitrosoguanidine was observed on the dishes containing 5, 7 and 10 g of butanol per liter. No growth occured on the dish containing 12 g of butanol per liter. On the dishes containing 5 and 7 g of butanol per liter, uniform growth of the strain was observed beyond the toxic zone. On the dish containing 10 g of butanol per liter, resistant mutants formed an aureole and eleven of them were purified by two passages on a dish containing 10 g of n-butanol per liter. With this n-butanol concentration, no growth of the wild strain on a dish was observed in the conditions of the experiment.

(2) Determination of the minimum inhibition concentration (MIC)

The resistance to n-butanol is an important property of the resultant mutants as shown by the following experiment. In this experiment, since a number of manipulations cannot be effected easily in the anaerobic chamber, there is used, outside of the chamber, pre-reduced media prepared in this chamber. The conventional culture media described above are propared in a somewhat different manner. The medium is prepared, a reduction indicator (resazurine) is added outside of the anaerobic charber, then the medium is heated up to discoloration of resazurine and the medium is then introduced into the anaerobic chamber; it is made into glass flasks stopped with a butyl stopper, then a metal cap is sealed with a holder. The flasks can be taken from the chamber and used as such after sterilization. There is effectively provided a medium under anaerobic atmosphere whose reduced state can be controlled by the color of reszurine.

These pre-reduced media are seeded with a syringe through the butyl rubber; all discharges and all additions are made in the same manner. These pre-reduced media have been used, inter alia, to determine the minimum inhibiting concentrations (MIC) of the mutant strains and of the *C. acetobutylicum* mother-strain for butanol. The latter, although volatile, does not suffer evaporation in the sealed flasks and the MIC can thus be determined with certainty.

Butanol at various concentrations is introduced into the flasks by means of a syringe. In the same manner, the strain to be tested is introduced into the flask containing 5 ml of medium in a proportion of 0.1 ml of a 12 hour-culture. After 24 h incubation at 32° C., the MIC is determined.

The results are given in Table 1 (the MIC determines the toxicity of a material on a given bacterial strain, the MIC corresponding to the first concentration of this material at which no bacterial growth is observed).

| STRAINS | BUTANOL CONCENTRATION (g/l) | | | | | | |
|---|---|---|---|---|---|---|---|
| | 0 | 5 | 10 | 13 | 15 | 18 | 20 |
| Mother-strain | + | + | + | − | − | − | − |
| Mutant No. 1 | + | + | + | + | − | − | − |
| Mutant No. 2 | + | + | + | + | + | − | − |
| Mutant No. 3 | + | + | + | + | + | − | − |
| Mutant No. 4 | + | + | + | + | + | + | − |
| Mutant No. 5 | + | + | + | + | + | + | − |
| Mutant No. 6 | + | + | + | + | − | − | − |
| Mutant No. 7 | + | + | + | + | − | − | − |
| Mutant No. 8 | + | + | + | + | − | − | − |
| Mutant No. 9 | + | + | + | + | − | − | − |
| Mutant No. 10 | + | + | + | + | + | − | − |
| Mutant No. 11 | + | + | + | + | + | − | − |

+: growth
−: no growth

It appears, as a rule, that the mutant strains have a greater resistance to butanol than the mother-strain.

The following experiment shows that the mutants resistant to n-butanol are also better producers of ABE than the mother-strain.

(3) Production of solvents with the mutants obtained

The production of solvents was determined in tubes containing 10 ml of an aqueous synthetic medium containing, per liter: $(NH_4)_2SO_4$, 3 g; $K_2HPO_4$, 0.5 g; $MgSO_4$, $7H_2O$, 10 mg; $MnCl_2$, $4H_2O$, 10 mg; $(NH_4)_2Mo_7O_{24}$, $H_2O$, 10 mg; $CaCo_3$, 3 g; yeast extract, 4 g; glucose, 60 g. The substrate was thus glucose. The cultures were effected in conventional conditions of sterility and in anaerobic conditions (handlings and incubation: 3 days at 32° C. in an anaerobic chamber). The results are given in the following Table 2:

TABLE 2

Production of solvents by the strain IFP 903 of *Clostridium acetobutylicum* and its mutants

| | ACETONE $g \times l^{-1}$ | BUTANOL $g \times l^{-1}$ | TOTAL SOLVENTS $g \times l^{-1}$ |
|---|---|---|---|
| Mother-strain | 2.6 | 7.8 | 10.4 |
| Mutant No. 1 | 5.0 | 11.6 | 16.6 |
| Mutant No. 2 | 3.0 | 9.1 | 12.1 |
| Mutant No. 3 | 3.9 | 10.2 | 14.1 |
| Mutant No. 4 | 4.4 | 10.6 | 15.0 |
| Mutant No. 5 | 3.9 | 10.7 | 14.6 |
| Mutant No. 6 | 4.1 | 10.5 | 14.6 |
| Mutant No. 7 | 4.4 | 12.3 | 16.7 |
| Mutant No. 8 | 4.4 | 11.3 | 15.7 |
| Mutant No. 9 | 3.3 | 9.4 | 12.7 |
| Mutant No. 10 | 4.8 | 12.5 | 17.3 |
| Mutant No. 11 | 4.1 | 12 | 16.1 |

EXAMPLE 2

Production of solvents in a fermentation vessel with the resultant mutants.

The wild strain of *C. acetobutylicum* (IFP 903) and the obtained mutants were grown in 6 liter fermentation vessels of the BIOLAFITTE type, containing 4 liter of a medium consisting of a Jerusalem artichoke pressing liquor diluted to half, chemically hydrolysed with sulfuric acid and neutralized with lime at pH 7.0. The mixture als comprised 3 g.l$^{-1}$ of $(NH_4)_2SO_4$ and 5 g.l$^{-1}$ of $CaCo_3$. The fermentation activity was measured with a meter by the volume of gas released and by the composition of the final solvent medium, determined by gas phase chromatography. The following Table summarizes the results obtained with the wild strain and with 4 mutants of high productivity after a fermentation of 36 h at 34° C., conducted in standard conditions of sterility and anaerobiose (the mixtures were deaerated by heating and maintained in an inert atmosphere).

| STRAIN (a) | ACETONE $g \times l^{-1}$ | BUTANOL $g \times l^{-1}$ | TOTAL SOLVENTS $g \times l^{-1}$ | GAS 1/1 OF THE MEDIUM |
|---|---|---|---|---|
| Mother-strain IFP 903 | 4.5 | 10.5 | 15.0 | 21.0 |
| Mutant No. 8 (IFP 904) | 10.0 | 15.0 | 25.0 | 37.0 |
| Mutant No. 5 | 9.0 | 13.6 | 22.6 | 33.5 |
| Mutant No. 4 | 8.0 | 13.4 | 21.4 | 31.5 |
| Mutant No. 11 | 8.4 | 13.3 | 21.7 | 32.5 |

(a) the mutant No. 8 was assigned reference No. 904 of the IFP collection.

The strains IFP 903 and 904 have been deposited on the 4th of Mar. 1982 at the American Type Culture Collection (ATCC) under the "Budapest Treaty in the International Recognition of the Deposit of Microorganism for the Purpose of Patent Procedure". The respective reference numbers ATCC 39 057 and 39 058 were assigned to them.

What is claimed is:

1. In a process comprising the production of an acetone-butanol mixture by the fermentation of sugars, the improvement wherein the fermentation is conducted with a microorganism of the strain of *Clostridium acetobutylicum* ATCC 39 058.

2. A process according to claim 1, wherein the microorganism is in the form of a biologically pure culture.

3. A biologically pure culture of *Clostridium acetobutylicum* ATCC 39058.

* * * * *